United States Patent [19]

Greunwald et al.

[11] Patent Number: 4,821,710

[45] Date of Patent: Apr. 18, 1989

[54] ADAPTOR TO ENDOTRACHEAL TUBE

[76] Inventors: Theodor Greunwald, 68 Horeb Str.; Yeshayahu Katz, 38 Hashomer Str., both of Haifa, Israel

[21] Appl. No.: 72,085

[22] Filed: Jul. 9, 1987

[30] Foreign Application Priority Data

Jul. 30, 1986 [IL] Israel .................................. 79566

[51] Int. Cl.$^4$ ............................................. A62B 27/00
[52] U.S. Cl. ................................................ 128/207.14
[58] Field of Search ..................... 128/202.22, 205.23, 128/207.14, 207.15

[56] References Cited

U.S. PATENT DOCUMENTS 4,691,701 9/1987 Williams ......................... 128/207.14

OTHER PUBLICATIONS

Murray et al., "Early Detection of Endotracheal Tube Accidents by Monitoring Carbon Dioxide Concentration in Respiratory Gas", *Anesthesiology*, 59, pp. 344–346, 1983, Ronald Miller, M.D., Editor.

Berman et al, "The Einstein Carbon Dioxide Detector", *Anesthesiology*, 60, pp. 613–614, 1984.

Moore, "Bupivacaine Toxicity and Bier Block: The Drug, The Technique, or The Anesthetist", *Anesthesiology*, 61, p. 782, 1984.

*Primary Examiner*—Gerald A. Michalsky
*Attorney, Agent, or Firm*—Morgan & Finnegan

[57] ABSTRACT

The present invention relates to a simple device for ensuring the correct placement of endotracheal intubation. According to the invention, there is a transparent adaptor suitable to be attached at one end to an endotracheal tube and at the other end to a mechanical respirator. Into the adaptor there is a solid support impregnated with a solution of at least two chemical compounds: organic amine and an indicator with a pK in the range of 8.0 to 10.5 of a concentration of at least 0.05% (wt. by volume) of the impregnation solution. The simplest form of solid support is a porous paper, such as filter paper, fiber or fabric. The correct insertion of the endotracheal intubation is noticed by the change in color of the impregnated solution onto the solid support. Optionally, the solution contains an inorganic alkali hydroxide, such as sodium hydroxide or potassium hydroxide, a humidifier and an organic solvent. It is universal and can be attached to any existent endotracheal tube.

12 Claims, No Drawings

ADAPTOR TO ENDOTRACHEAL TUBE

The present invention relates to a method and device for the detection of the correct location of endotracheal tube. More particularly, the invention relates to a simple device for ensuring a correct endotracheal intubation.

BACKGROUND OF THE INVENTION

As known, intubation is defined as the introduction of a plastic tube called endotracheal tube into the trachea in order to ventilate a patient. One of the main problems in performing this procedure, is the location of the tube within the trochea and not the esophagus. A wrong intubation within the esophagus, means death because of hypoxia. The old methods for ensuring the proper location of the endotracheal tube, consist in auscultation over the stomach, which should reveal characteristic sounds if the tube is in the esophagus. However, transmission of sounds to the lungs created by ventilation through an esophageal intubation may result in a false feeling of security. Furthermore, there are certain circumstances, particularly in battle field injuries and road accidents where the multiple trauma precludes abdominal auscultation. In a very recent paper (Anesthesiology, 59, p.344-6, 1983) the detection of endotracheal tube accidents by monitoring carbon dioxide concentration in respiratory gas was mentioned. Based on this approach, it was suggested (Anesthesiology, 60, 613-4) the use of the Einstein carbon dioxide detector based on the chemical attributes of cresol red and phenophthalein indicators which change colors in the presence of an increased concentration of hydrogen ions resulting from the carbonic acid obtained from the carbon dioxide in the respiratory gas. The indicators are used in the form of a solution of 3 mls of phenophthalein and 3 mls cresol present in a chamber through which the catheter end of the mucus trap is introduced. Although the clinical application of the Einstein device, is mentioned by the authors to be simple, it has the main disadvantage in the poor reliability of the correct location. This is a consequence of the inaccurate result from the change in the indicator colour, in view of the low acidity level imparted by the carbonic acid. It has also been stated (Anesthesiology, 61:782, 1984) that the device described above "is awkward, messy and dependent on prior preparation". In this communication it is suggested to utilize an expensive electronic carbon dioxide detector device. The device aspirates gas thhrough a fine plastic capillary that can be attached to the elbow connector of the anesthesia breathing circuit. However, such devices are impractical in every day use, because they need electric power supply, are difficult to operate and can not be consumed by underdeveloped countries.

SUMMARY OF THE INVENTION

It is an object of the present invention to provide a simple device for ensuring the correct placement of endotracheal intubation. It is another object of the present invention to provide a simple and unexpensive device for ensuring the correct placement of endotracheal intubation which can be easily utilized even by unskilled persons. Thus, the invention consists in a transparent adaptor suitable to be attached at one end to an endotracheal tube and at the other end to a mechanical respirator, the device containing a solid support impregnated with a mixture of at least two chemical compounds: (a) organic amine(s) and (b) an indicator with a pK in the range of between 8.0 and 10.5 of a concentration of at least 0.05% (weight by volume) of the constituents in the impregnatory solution.

The simplest solid support is a porous paper, fiber or fabric, although in principle one can utilize other solid support which is porous and do not disintegrate, such as pellets or balls. In particular preferable is a laboratory filter paper such as Whatman (Registered Trade Mark) paper Number 1, 2 or 3.

The organic amine present in the impregnating solution has an important role assuring a rapid absorption of the carbon dioxide and thus ensuring the reliable results. In particular suitable are organic amines selected from ethylene diamine, ethanol amine, butyl amine or mixtures thereof.

In addition to the amine and the indicator, it is suggested to incorporate an inorganic alkali hydroxide such as NaOH, KOH or LiOH, which renders to the solution the high pH (about 10 to 12) and also a good and stable colour to the indicator present in the absorption solution. The concentration of the amine is not critical, the preferred concentration being between 2-25% by volume of the solution. The indicator to be present in the impregnation solution, can be any acid-base indicator, or any mixture thereof, possessing a pK between 8.0 to 10.5, so that it will change its colour upon the reaction of the carbon dioxide with the impregnated solid support. Typical examples of suitable indicators are Thymol blue, Cresolphthalein, Cresol red, etc. According to a most preferred embodiment, the impregnation solution contains also a humidifier constituent which will assure a minimum water content in the final air dried porous support to be used. The minimum water content, will facilitate the diffusion of the carbon dioxide gas and its reaction with the chemicals adsorbed on the porous support. A preferred humidifier constituent is glycerin in a concentration of 5-15% by volume of the solution to be impregnated.

Another optional ingredient preferable to be present in the impregnation solution, is an organic solvent such as a lower alcohol (ethanol, methanol) its purpose being to render a better solubility of the organic ingredients in the solution. The concentration of the solvent is generally between 10% to 50% by volume of the total solution.

The adaptor to be used in the present invention, containing the porous support with the adsorbed solution, can be utilized with any endotracheal tube. As known, the internal diameter of the tube varies from 2.5 to 10 mm, being packed in a sterile seal with its adaptor to fit the corresponding diameter of the tube. Prior to intubation, the tube has to be connected to the adaptor.

The invention is based on the fact that in every breath, the expired gas contains about 4-6% carbon dioxide, whereas air or gas from anesthetic circuit contains negligible amounts of it. Therefore esophageal intubation will be substantially free of carbon dioxide and accordingly free of carbonic acid i.e. acidic constituent.

The adaptor can be made of any plastic material or glass, preferably of an unbreakable type, the mandatory requirement being its transparency, to enable an easy observation of the change in colour.

The adaptor according to the present invention has been described in connection with its use in endotracheal intubation, but can also be successfully utilized also for tracheostomy, when the tube is inserted through the throat.

Among the main advantages of the adaptor according to the present invention, the following can be enumerated:

The adaptor does not require any additional equipment to function or to be evaluated.

The adaptor is universal, fitting all size tubes.

The adaptor can be also utilized to detect malfunction of anesthetic machines in operating rooms.

The adaptor's production costs are very low and therefore its cost-effectiveness is very high.

The adaptor has particular use in military application, in view of the intubations which are carrier out in the battle field by inexperienced people under difficult conditions. The same situation might be encountered in many emergencies cases when para-medical personnel has to perform such operation.

The invention will be hereafter illustrated by the following Examples, being clearly understood that these Examples are presented for a better understanding of the invention, without being limited thereto.

EXAMPLE 1

A piece of Whatman filter paper (Number 2) was impregnated with an impregnation solution consisting of: 2% aminoethanol and 0.1% of a mixture of o-cresolphthaleimine - thymol blue (2:1 ratio). The correct insertion of the endotracheal intubation was noticed by the change in colour of the filter paper from violet to off-white after 4 breathing cycles.

EXAMPLE 2

The experiment as in Example 1 was repeated but in this case the impregnating solution consisted of 10% ethylene diamine and 0.1% of Cresol red indicator. The proper insertion of the endotrocheal tube was noticed by the change in colour after 5-6 breathing cycles from violet-red to off-white.

EXAMPLE 3

The experiment as in Example 1 was repeated, but in this case the filter paper was replaced by a piece of a porous cotton fiber cloth (FISCHER brand 6-667) and the impregnating solution consisted of 5% Triethylamine and 0.1% of Thymolphthaleine indicator. The correct insertion of the endotracheal tube was noticed by the change in colour after 5-6 breathing cycles from Violet-red to off-white.

EXAMPLE 4

A piece of Whatman filter paper (Number 2) was impregnated with a 0.02 M solution of LiOH containing: 20% ethanol, 5% by volume of 2-aminoethanol; 0.2% by weight of a mixture of o-cresolphthaleimine - thymol blue (4:1 ratio) indicator mixture, and 10% by volume of glycerin. The correct insertion of the endotracheal intubation was noticed by the change in colour of the filter paper (located into the adaptor) with the above adsorbed chemicals, from violet to white, after 1 breathing cycle.

We claim:

1. A transparent adaptor suitable to be attached at one end to an endotracheal tube and at the other end to a mechanical respirator, the adaptor containing a solid support impregnated with a solution of at least two chemical compounds; (a) organic amine and (b) an indicator with a pK in the range of 8.0 to 10.5 having a concentration of at least 0.05% (weight by volume) of the impregnation solution.

2. A transparent adaptor according to claim 1, wherein said impregnation solution contains in addition an alkali selected from the group consisting of NaOH, KOH, or LiOH.

3. A transparent adaptor according to claim 1, wherein said impregnation solution contains a humidifier.

4. A transparent adaptor according to claim 3, wherein said humidifier is glycerin.

5. A transparent adaptor according to claim 3, wherein the amount of the humidifier is between 5% to 15% by volume of the solution.

6. A transparent adaptor according to claim 1, wherein said organic amine is a mixture of organic amines.

7. A transparent adaptor according to claim 6, wherein said organic amine is selected from ethylene diamine, ethanol amine, butyl amine or mixtures thereof.

8. A transparent adaptor accoring to claim 6, wherein the amount of the organic amine is between 2% to 25% by volume of the impregnation solution.

9. A transparent adaptor according to claim 1, wherein said solid support is in the form of porous paper.

10. A transparent adaptor according to claim 1, wherein said solid support is in the form of porous fabric.

11. A transparent adaptor according to claim 1, wherein an organic solvent is present in the impregnation solution.

12. A transparent adaptor according to claim 11, wherein said organic solvent is selected from ethanol or methanol.

* * * * *